(12) United States Patent
Anderson

(10) Patent No.: US 10,004,534 B2
(45) Date of Patent: *Jun. 26, 2018

(54) SEALED DISTAL END PROSTHESIS INSERTION BAG

(71) Applicant: Robert G. Anderson, Aledo, TX (US)

(72) Inventor: Robert G. Anderson, Aledo, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/666,367

(22) Filed: Aug. 1, 2017

(65) Prior Publication Data

US 2018/0070984 A1 Mar. 15, 2018

Related U.S. Application Data

(63) Continuation of application No. 15/261,196, filed on Sep. 9, 2016, now Pat. No. 9,336,973.

(51) Int. Cl.
| | | |
|---|---|---|
| *A61F 2/12* | (2006.01) | |
| *A61B 17/34* | (2006.01) | |
| *A61F 2/00* | (2006.01) | |
| *A61B 17/02* | (2006.01) | |
| *A61B 17/00* | (2006.01) | |

(52) U.S. Cl.
CPC ........ *A61B 17/3468* (2013.01); *A61F 2/0095* (2013.01); *A61B 17/02* (2013.01); *A61B 2017/00796* (2013.01); *A61F 2/12* (2013.01); *A61F 2230/0067* (2013.01)

(58) Field of Classification Search
CPC .......................................... A61F 2/12
USPC ........................................ 623/7–8
See application file for complete search history.

(56) References Cited

U.S. PATENT DOCUMENTS

| | | |
|---|---|---|
| 4,035,850 A | 7/1977 | Cresswall |
| 4,641,648 A | 2/1987 | Shapiro |
| 4,995,906 A | 2/1991 | Iwasaki et al. |
| 5,571,178 A | 11/1996 | Ledergerber |
| 5,723,006 A | 3/1998 | Ledergerber |
| 5,782,913 A | 7/1998 | Schindler et al. |
| 8,206,443 B2 | 6/2012 | Preissman |
| 8,211,173 B2 | 7/2012 | Keller et al. |
| 8,313,760 B2 | 11/2012 | Hunter |

(Continued)

FOREIGN PATENT DOCUMENTS

WO     2013122568 A1     8/2013

OTHER PUBLICATIONS

Richard A. Mladick, M.D., F.A.C.S. "No-Touch" Submuscular Saline Breast Augmentation Technique, Aesthetic Plastic Surgery, 17:1 83-192, 1993, New York, NY.

(Continued)

*Primary Examiner* — Suzette J Gherbi
(74) *Attorney, Agent, or Firm* — Kirby Drake

(57) ABSTRACT

An apparatus and method for inserting prosthesis implants into a patient pocket. The apparatus has multiple openings including a prosthesis opening, a proximal opening, and a small opening to receive a lubricating fluid. The prosthesis bag is a container with a wide sealed distal end and passage to a narrow apex. The apparatus reduces infection; eases insertion and placement of a cohesive silicone gel implant; and reduces complications. In use, the prosthesis bag is placed through the patient incision while allowing the bag to be manipulated to force the prosthesis into a surgical pocket of a patient.

5 Claims, 13 Drawing Sheets

(56) References Cited

U.S. PATENT DOCUMENTS

| | | | |
|---|---|---|---|
| 8,550,090 B2 | 10/2013 | Keller et al. | |
| 8,555,893 B2 | 10/2013 | Keller et al. | |
| 8,641,758 B1 | 2/2014 | Anderson | |
| D736,372 S | 8/2015 | Anderson | |
| D738,490 S | 9/2015 | Anderson | |
| D742,509 S | 11/2015 | Anderson | |
| D752,739 S | 3/2016 | Anderson | |
| 9,474,593 B2* | 10/2016 | Anderson | A61F 2/12 |
| 9,782,251 B2* | 10/2017 | Anderson | A61F 2/12 |
| 9,808,285 B2* | 11/2017 | Anderson | A61B 17/3468 |
| 2007/0276484 A1 | 11/2007 | Abell et al. | |
| 2009/0204107 A1 | 8/2009 | Keller et al. | |
| 2010/0280610 A1* | 11/2010 | Preissman | A61F 2/12 623/8 |
| 2011/0035003 A1 | 2/2011 | Preissman | |
| 2011/0082546 A1* | 4/2011 | Freund | A61F 2/12 623/8 |
| 2011/0218624 A1 | 9/2011 | Preissman | |
| 2012/0185042 A1 | 7/2012 | Preissman | |
| 2012/0259414 A1 | 10/2012 | Preissman | |
| 2013/0073040 A1 | 3/2013 | Preissman | |
| 2014/0074235 A1 | 3/2014 | Keller et al. | |
| 2014/0074236 A1 | 3/2014 | Keller et al. | |
| 2014/0148901 A1 | 5/2014 | Anderson | |
| 2014/0228951 A1* | 8/2014 | Zochowski | A61F 2/12 623/8 |
| 2015/0126812 A1 | 5/2015 | Anderson | |
| 2015/0297339 A1 | 10/2015 | Placik et al. | |
| 2015/0374478 A1 | 12/2015 | Anderson | |
| 2016/0038275 A1* | 2/2016 | Preissman | A61F 2/12 623/8 |
| 2016/0095697 A1* | 4/2016 | Anderson | A61F 2/12 623/8 |
| 2016/0374720 A1 | 12/2016 | Anderson et al. | |
| 2017/0014158 A1* | 1/2017 | Anderson | A61B 17/02 |
| 2017/0100233 A1* | 4/2017 | Zochowski | A61F 2/12 |
| 2017/0354488 A1* | 12/2017 | Anderson | A61F 2/0095 |

OTHER PUBLICATIONS

Richard A. Mladick, M.D., F.A.C.S. "Significance of *Staphylococcus epidermidis* Causing Subclinical Infection," Plastic & Reconstructive Surgery, Apr. 15, 2005, vol. 115, Issue 5, pp. 1426-1427.

Richard A. Mladick, M.D., F.A.C.S.. "Prevention of Capsular Contracture," Plastic & Reconstructive Surgery, May 1999, vol. 103, Issue 6, pp. 1773-1774.

Thomas M. Biggs, M.D., "Prefilled Saline Breast Implants Offer Significant Advantages," Aesthetic Surgery Journal, Sep. 1999, vol. 19, No. 5424.

Mitchel H. Brown, M.D., M.Ed., "Cohesive Silicone Gel Breast Implants in Aesthetic and Reconstructive Breast Surgery," Plastic & Reconstructive Surgery, Sep. 1, 2005, vol. 116, Issue 3, pp. 768-779.

"International Search Report," for PCT Patent Application No. PCT/US17/52996, dated Dec. 11, 2017, 2 pages.

"Written Opinion of the International Search Authority," for PCT Patent Application No. PCT/US17/52996, dated Dec. 11, 2017, 4 pages.

\* cited by examiner

SEALED DISTAL END PROSTHESIS INSERTION BAG

CROSS REFERENCE TO RELATED APPLICATION

This application is a continuation of U.S. Non-Provisional patent application Ser. No. 15/261,196 filed on Sep. 9, 2016, entitled "Sealed Distal End Insertion Bag," which is incorporated by reference in its entirety.

FIELD OF THE DISCLOSURE

The present disclosure relates to the apparatus and method of safely inserting a prosthesis into a human body.

BACKGROUND

Breast implants are a manufactured prosthesis used in cosmetic and reconstructive surgery. A breast implant has an outer casing or membrane that is filled with a fluid such as saline or a gelatinous cohesive silicone.

Only about thirty percent (30%) of breast implant procedures today use an insertion device. An insertion device shortens the duration of the surgical procedure and improves the surgery outcome. In regard to a cohesive silicone gel implant, without an insertion device, the surgeon makes the incision, creates a pocket for the implant, retracts the incision and then manually pushes the implant across the skin through the incision into the pocket.

Different than a silicone gel filled implant, a saline implant is inserted into the pocket in an empty configuration. Once placed in the pocket, the surgeon takes the additional step of filling the implant with a saline solution using a fill tube.

The incision is made in one of four places: in the armpit, in the breast fold, in the navel, or around the areola. Except for the navel insertion site, one incision is made for each implant. It is preferable that the incision be as short as possible. Shorter incisions are less unsightly. This goal of a shorter incision is easier to accomplish with a saline implant. A saline implant is relatively easy to insert through a short incision, because the implant is unfilled and therefore small in size as it passes through the incision. For these inflatable implants, the surgeon rolls up the implant like a cigar and pushes it through the incision into the pocket. In contrast, silicone implants are prefilled by the breast implant manufacturer resulting in a more difficult and complication-susceptible operation. For these pre-filled implants, the procedure requires a longer incision length.

After the initial incisions, the surgeon dissects a path through the tissue to the desired destination of the implant. Once that path has been created, a pocket is created for the implant superficial or deep to the pectoralis major muscle. The pocket may be formed in one of two places under the breast: subglandular (between the breast tissue and pectoralis major muscle) or subpectoral (under the pectoralis major muscle). Subglandular places the prosthesis directly behind the mammary gland and in front of the pectoralis major muscle. Subpectoral places the implant partially under the pectoralis major muscle. Due to the shape of the pectoralis major muscle, a portion of the implant is not covered by the muscle.

Secondary surgery is common for patients with breast implants. In particular, patients with breast implants may require surgery to change the placement (from subglandular to subpectoral or vice versa), correct palpable folding of the implant, remove a ruptured implant, treat infection, bleeding, breast pain, contracted scar tissue forming around the implant (capsular contracture) and collections of fluid around the implant. These additional surgeries have risks due to anesthesia, infection and bleeding. The overall secondary operation complication rate is almost 20% for silicone gel breast augmentation within 3 years of the initial operation and up to 36-45% by 10 years from the initial breast implant surgery. The majority of re-operations are related to capsular contracture, implant rupture (leakage), bleeding or infection or implant malposition.

Cellulitis, a skin-based infection occurring in 2%-4% of patients, is usually from bacteria normally present on the skin. Symptoms of infection include fever, pain, swelling and redness. To reduce infection, surgeons give a single dose of antibiotics before the surgery, and use an antibiotic solution in the wound before implant placement. The antibiotic solution may double as the lubrication to allow easier insertion of the implant into the pocket. However, surgeons can bring the rate of capsular contracture and infection down further by preventing the implant from touching the patient's skin.

The implant insertion devices heretofore known suffer from a number of disadvantages:

1. The device has two openings. The larger opening through which the implant is placed in the device is unsealed and the device cannot be sealed closed which allows the implant to inadvertently slip out of the larger open end of the device resulting in dropping the implant and/or contaminating the implant with skin bacteria.
2. The high cost of current implant devices encourages re-use despite the manufacturer recommendation not to do so.

SUMMARY

Embodiments of the present disclosure may provide a system and method to insert a prosthesis into a patient. The prosthesis insertion bag is a container with a wide sealed distal end and passage to a narrow opening. The device maintains the implant in the interior and only allows exit through the proximal end. Accordingly, besides the objects and advantages of the system for a breast implant insertion device described above, several objects and advantages of the present disclosure are:

a) to provide a device that only permits the implant to exit through the proximal end;
b) to provide a simplified insertion method;
c) to provide the means to reduce anesthesia time;
d) to provide a single device that fits all sizes of implants;
e) to provide an easier manipulation of the implant.
f) to provide an opening for instillation of a lubricant and/or sterilizing liquid.

Further objects and advantages of the present disclosure will become apparent from a consideration of the drawings and the ensuing description of the drawings.

DRAWING FIGURES

The accompanying drawings, which are incorporated in and constitute a part of this specification, illustrate embodiments of the present disclosure and together with the description, serve to explain the principles of this disclosure.

Figure 1:
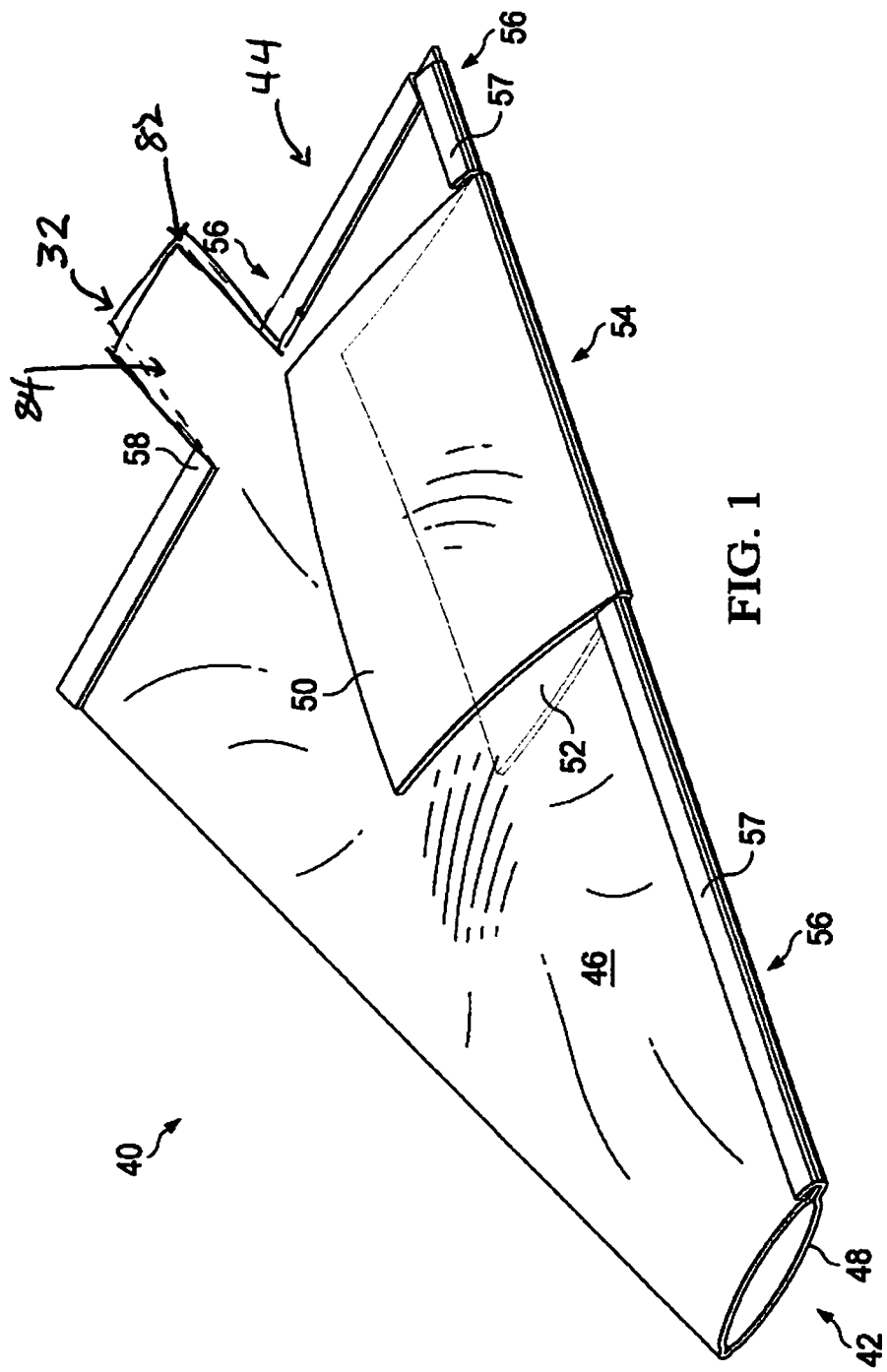
FIG. 1 depicts a top-side perspective view of a prosthesis bag according to an embodiment of the present disclosure.

KEY TERMS distal: the most distant portion from the point of attachment to the body
inferior: closer to the feet
lateral: a position substantially located in any side of the longitudinal position of a patient's supine position
longitudinal: a lengthwise, or the longest, direction related to the patient's supine position
proximal: the closest portion from the point of attachment to the body
superior: closer to the head of the body

REFERENCE NUMERALS IN DRAWINGS 10 patient
20 patient's incision, opening
22 patient's breast
24 patient's implant pocket
28 patient's skin tissue
30 prosthesis, implant
32 lubricant instillation opening
40 prosthesis bag, bag
42 proximal end, proximal opening
44 sealed distal end
46 base fold
48 initial fold
50 exterior tab
52 internal tab
54 prosthesis opening
56 seal folds
57 tab-side seal tuck
58 distal end seal tuck
60 lubricant
70 retractor
72 retractor handle
74 retractor handle proximal end
76 retractor proximal end lip
80 distal pouch
82, 84 lubricant instillation tabs, flaps

DETAILED DESCRIPTION

Referring now to FIG. 1, the top side perspective view of prosthesis bag 40 may be manufactured with a sheet material such as plastic or a flexible, surgical-grade nylon. The plastic may be strengthened or reinforced with fibers. Prosthesis bag 40 may be clear, or semi-transparent, to allow observation of prosthesis 30 moving from bag 40 into patient pocket 24.

Prosthesis bag 40 has multiple openings including proximal opening 42 for inserting into incision 20, prosthesis opening 54, surrounded by exterior tab 50 and internal tab 52, for inserting prosthesis 30 into prosthesis bag 40, and lubrication instillation opening 32 surrounded by flaps 82,84. FIG. 1 shows tabs 50, 52 located proximally to distal end 44 and internal tab 52 pushed through prosthesis opening 54, to prevent the implant from passing to the outside of prosthesis bag 40, and exterior tab 50 folded over prosthesis opening 54. Exterior tab 50 may be folded and held in place by the surgeon's hand, friction or attached by glue, adhesive, heat bond, surgical tape or other coupling mechanism. While FIG. 1 shows both tabs 50, 52 folded into the working position, exterior tab 50 and internal tab 52 would initially be presented to the surgeon with both tabs 50, 52 outside of prosthesis bag 40 and surrounding prosthesis opening 54. While the preferred embodiment shows different sized tabs 50, 52 to distinguish exterior tab 50 from internal tab 52, tabs 50, 52 may be of the same size in some embodiments of the present disclosure.

Prosthesis bag 40 may be assembled using seal tucks 56 which comprise two (2) tab-side seal tucks 57, and one (1) distal end seal tuck 58. In a preferred embodiment, the assembly may be done prior to packaging and shipping to the surgeon. In an alternate embodiment, seal tucks 56 may be sealed to the base fold 46 by the patient's 10 operating team. See FIG. 9B for additional illustration of the assembly using seal tucks 56.

Prosthesis bag 40 prevents breast implant 30 from touching the patient's skin tissue 28, prevents the implant 30 from inadvertently exiting the chamber, and prevents damage to implant 30 during implant 30 insertion. Prosthesis bag 40 may be manufactured to accommodate any breast implant 30 shape, volume, and diameter. The prosthesis bag proximal end 42 may be trimmed by the surgeon to accommodate different size implants 30. The manufacturer may suggest specific skin incision 20 lengths to allow insertion of implant 30 through bag 40 into incision 20. The specifications take the burden off the surgeon to try to make shorter incisions 20.

Figure 2:
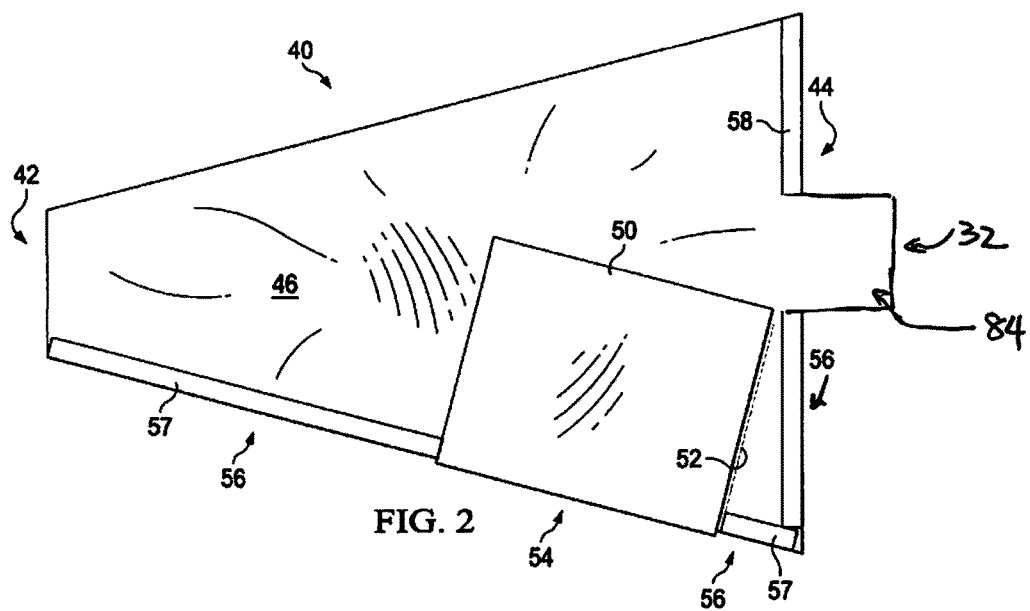
FIG. 2 depicts a top view of a prosthesis bag according to an embodiment of the present disclosure.
Figure 3:
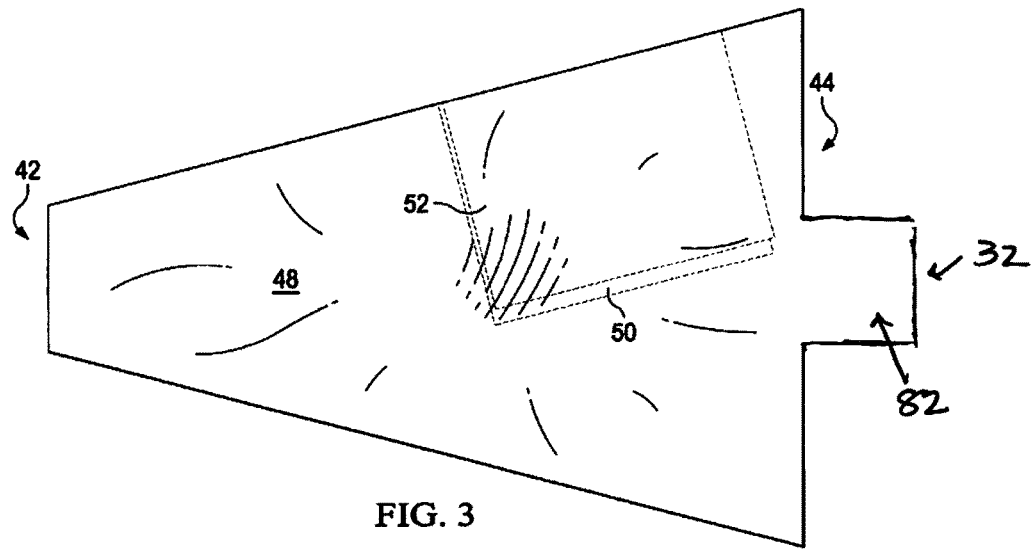
FIG. 3 depicts a bottom view of a prosthesis bag according to an embodiment of the present disclosure.

FIGS. 2-3 shows a top and bottom view, respectively, of the manufactured version of prosthesis bag 40 once initial fold 48 is folded over base fold 46 along the abutted seam and three (3) seal tucks 56 are adhered to base fold 46. Manufactured bag 40 comprises initial fold 48 partially sealed on the periphery to base fold 46, proximal opening 42, sealed distal end 44, prosthesis opening 54, exterior tab 50 and internal tab 52. Seal folds 56 comprise tab side seal tucks 57 and distal end seal tuck 58. Internal tab 52 may be folded through prosthesis opening 54 and exterior tab 50 then may be folded over prosthesis opening 54 to secure opening 54 and prevent the inadvertent exit of implant 30.

Figure 4:
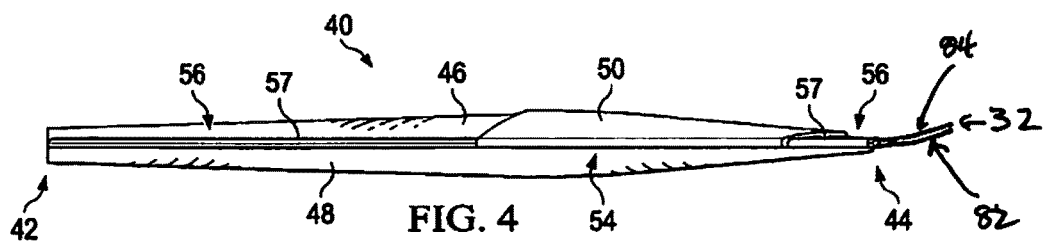
FIG. 4 depicts a right view of a prosthesis hag according to an embodiment of the present disclosure.
Figure 5:
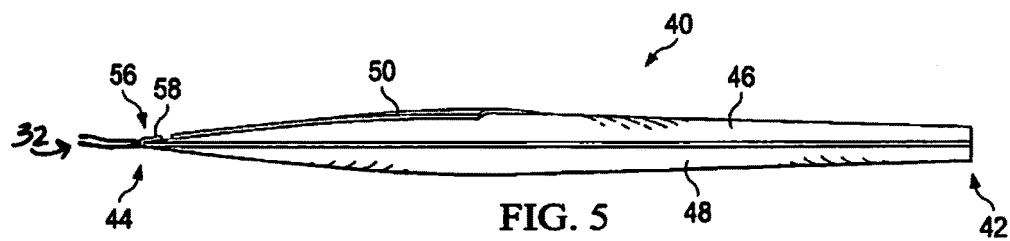
FIG. 5 depicts a left view of a prosthesis bag according to an embodiment of the present disclosure.
Figure 6:
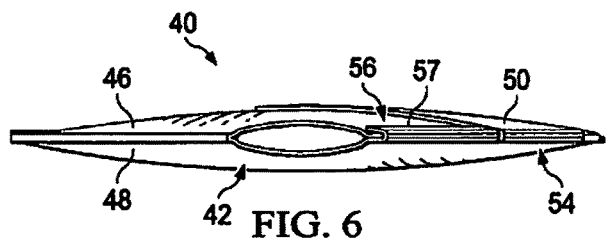
FIG. 6 depicts a proximal end view of a prosthesis bag according to an embodiment of the present disclosure.
Figure 7:
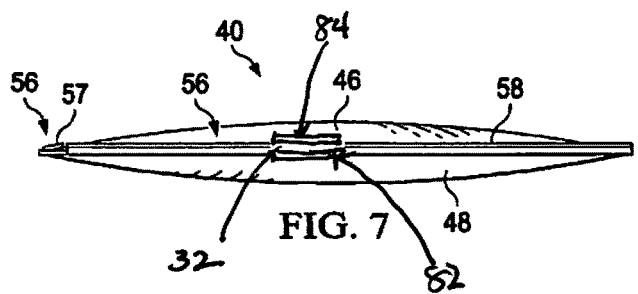
FIG. 7 depicts a distal end view of a prosthesis bag according to an embodiment of the present disclosure.

FIG. 4 shows the right side of prosthesis bag 40 with exterior tab 50 folded over base fold 46. FIG. 5 illustrates prosthesis bag 40 with proximal opening 42 located parallel to distal end seal tuck 58. FIG. 6 shows proximal end 42 with proximal opening 42. FIG. 7 illustrates distal end 44 with distal end seal tuck 58.

Figure 8:
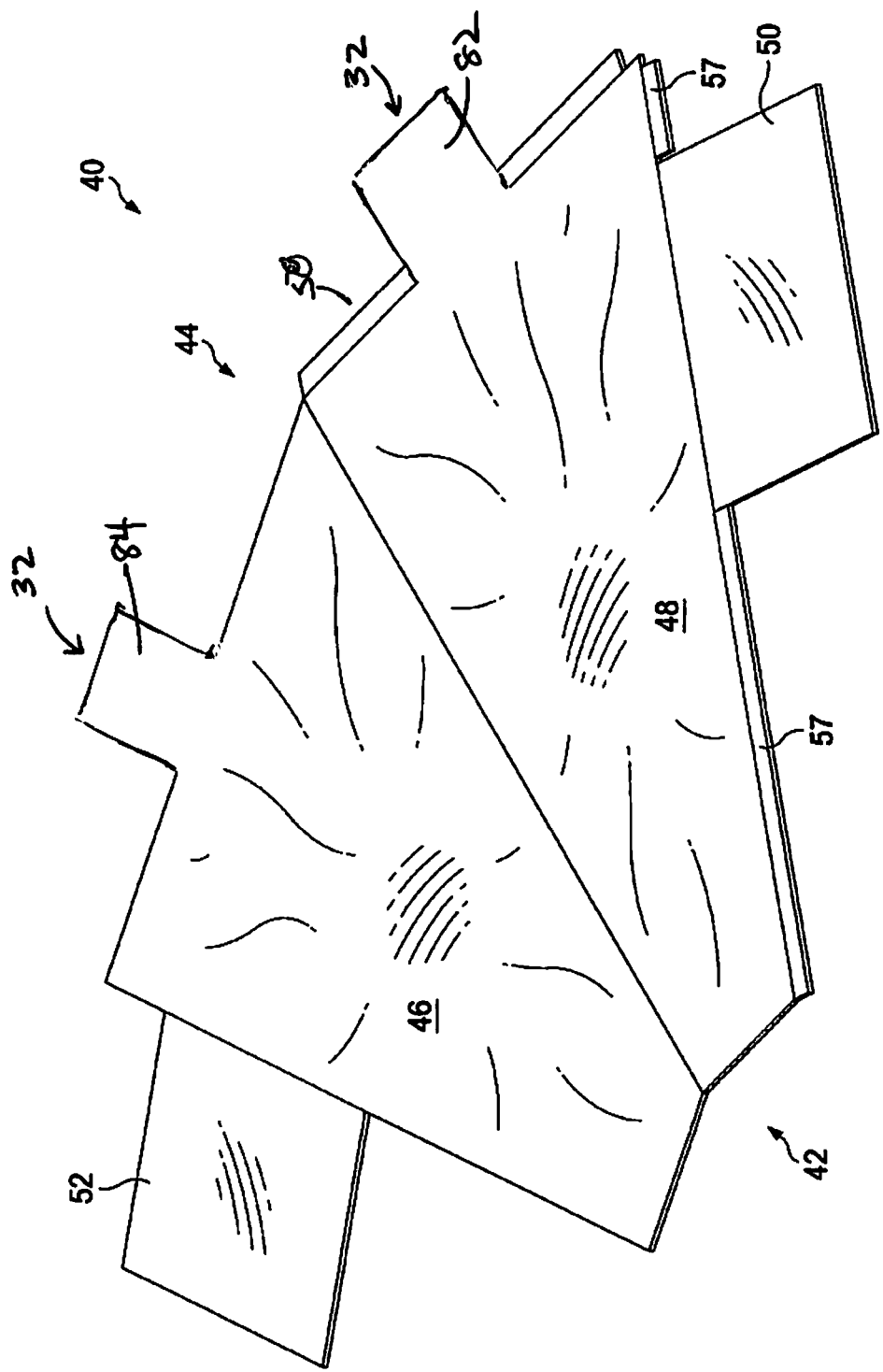
FIG. 8 depicts a top side perspective view of an unassembled a prosthesis bag attached to the initial fold according to an embodiment of the present disclosure.

Turning to FIG. 8, the illustration depicts a perspective view of unassembled prosthesis bag 40. Prosthesis bag 40 comprises two folds 46, 48 with opposing prosthesis insertion tabs 50, 52 and opposing lubricant instillation tabs 82,84. In a preferred embodiment, tabs 50, 52 may be located distally and opposing the abutted sides of manufactured prosthesis bag 40. In a preferred embodiment, as shown in FIGS. 3-4D base fold 46 is manufactured abutted against initial fold 48 along either edge opposing the tabbed side of folds 46, 48. In a second embodiment, initial fold 48 and base fold 46 would be separately manufactured and assembled together at a later stage.

In the preferred embodiment, prosthesis bag 40 would be folded along an abutted edge and manufactured with three seal tucks 56 along:
a. initial fold's 48 sealed distal end 44 from the abutted side to the tab side;
b. initial fold's 48 tab-side edge from exterior tab 50 to proximal end 42;
c. initial fold's 48 tab-side edge from exterior tab 50 to sealed distal end 44.

In another embodiment, seal tucks 56 may be replaced with a simple seam along the edges to bind initial fold 48 and base fold 46 with glue, adhesive, heat bond, surgical tape or other coupling mechanism.

Figure 9A:
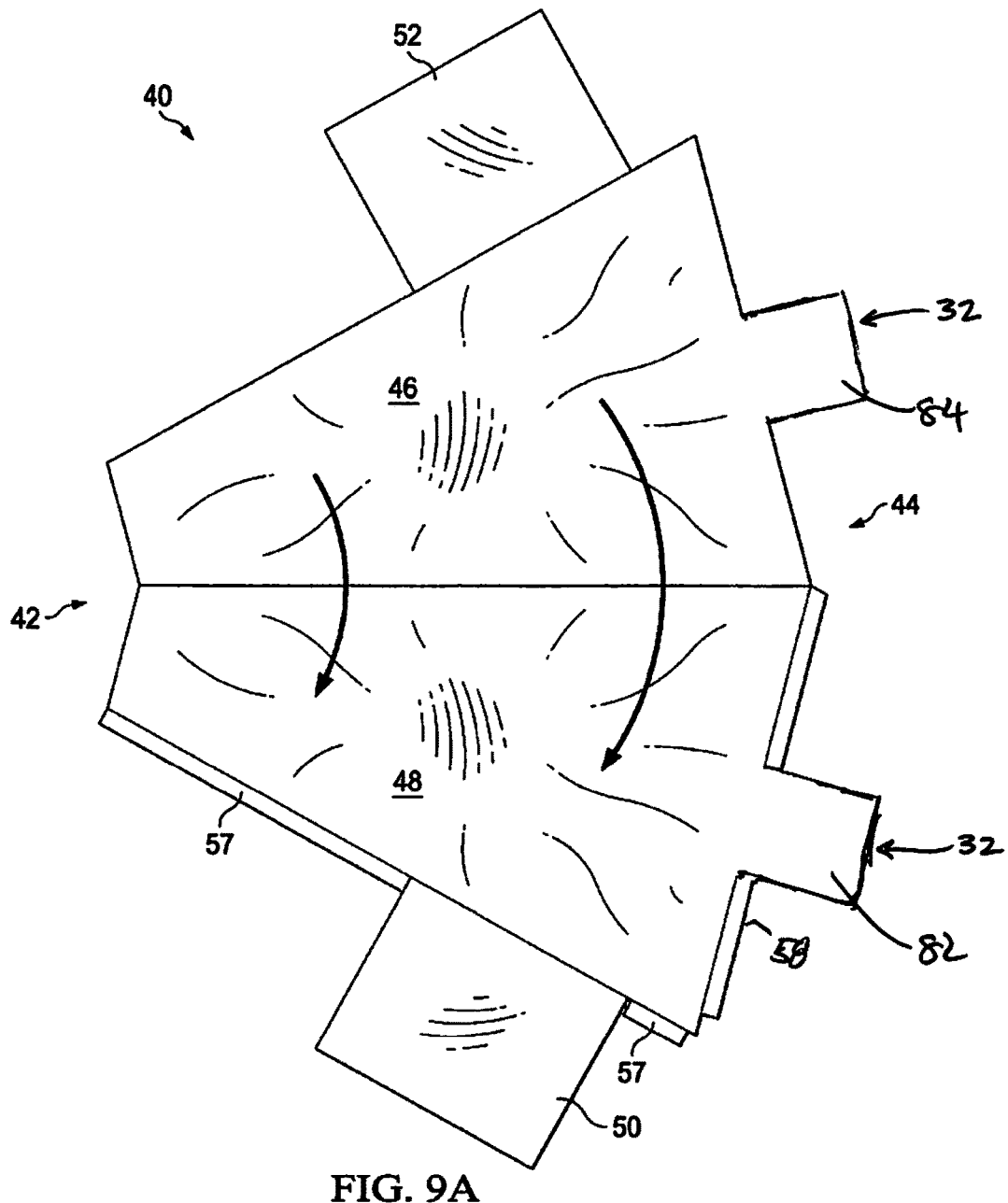
FIG. 9A depicts a top view of a prosthesis bag being folded along the abutted edges according to an embodiment of the present disclosure.

FIGS. 9A to 9D show the assembly of prosthesis bag 40. In FIG. 9A, the pattern is folded along the abutted edge so that base fold 48 and initial fold 46 are stacked over each other with tabs 50, 52 pointing to the side and in the same direction.

Figure 9B:
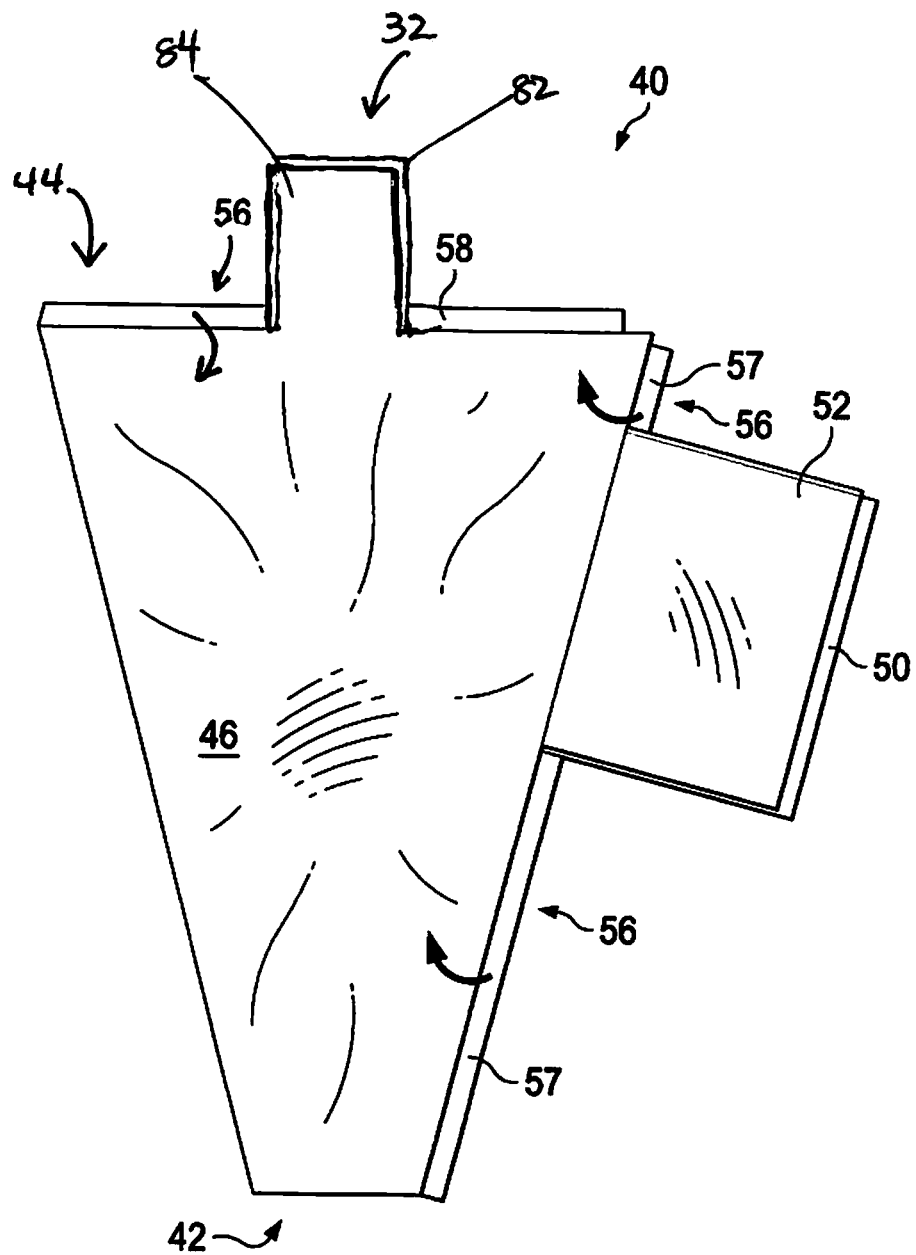
FIG. 9B depicts a top view of a prosthesis bag showing the base fold assembled over the initial fold according to an embodiment of the present disclosure.

Then in FIG. 9B, seal tucks 56 are folded over opposing fold 46, 48 and sealed to opposing fold 46, 48 with any desired manufacturing sealing technique. The tabs remain unfolded until breast implant 30 and lubricant 60 are placed inside bag 40.

Figure 9C:
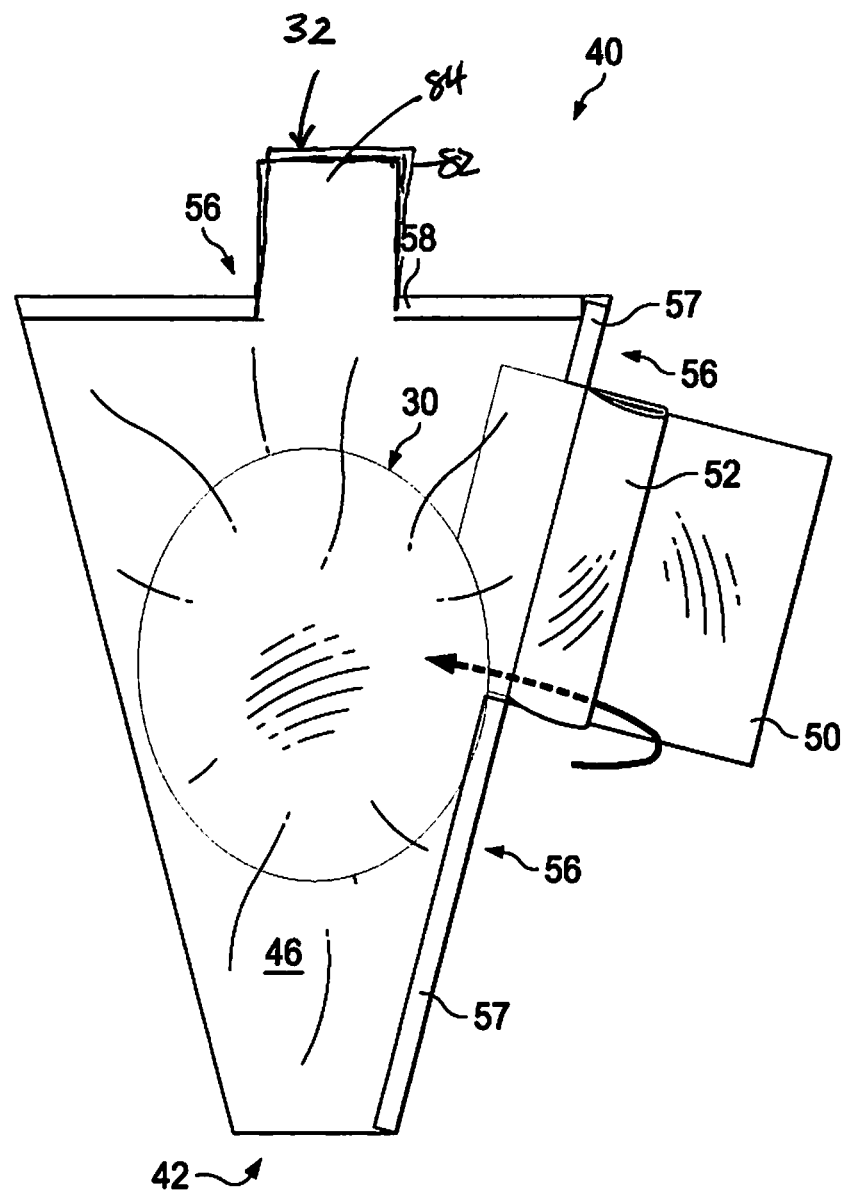
FIG. 9C depicts a top view of a prosthesis bag with the internal tab folded through prosthesis opening after the prosthesis is inserted according to an embodiment of the present disclosure.

With breast implant 30 in place inside prosthesis bag 40, in FIG. 9C, internal tab 52 is pushed through prosthesis opening 54. Internal tab 52 prevents implant 30 from inadvertently ejecting through prosthesis opening 54 during the operation.

Figure 9D:
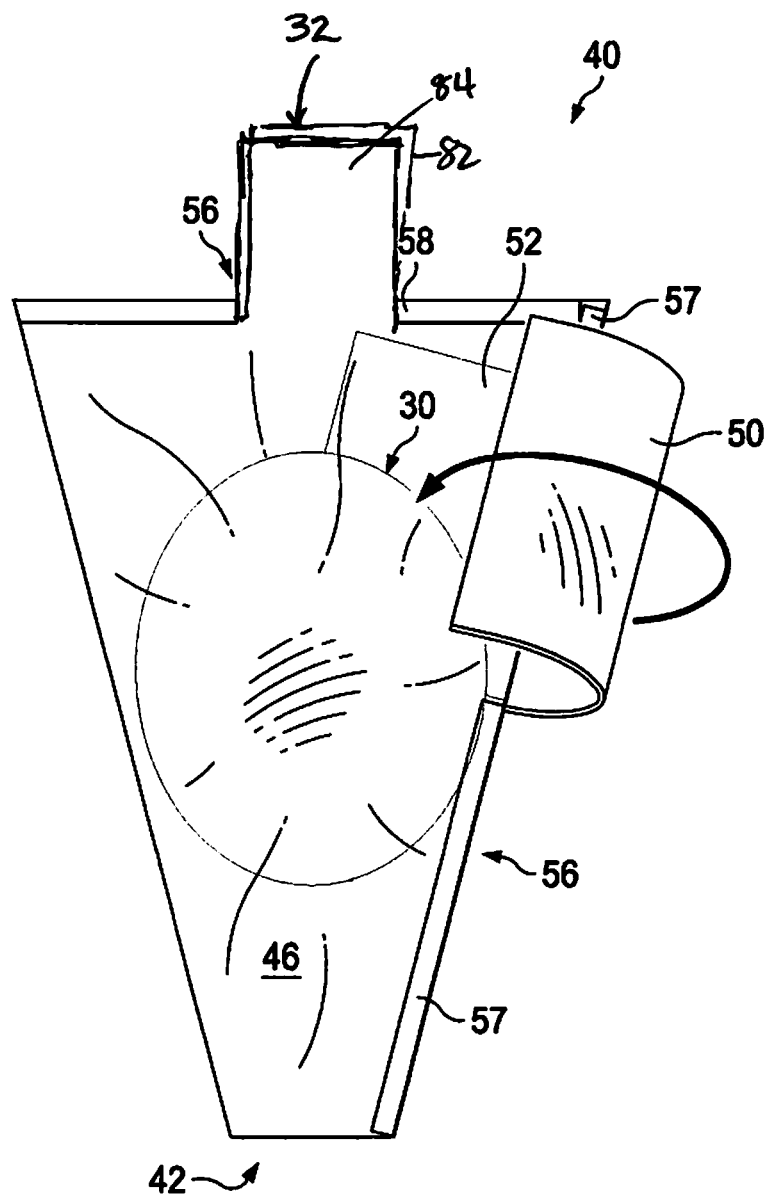
FIG. 9D depicts a top view of a prosthesis bag with the exterior tab being folded over the prosthesis opening according to an embodiment of the present disclosure.

In FIG. 9D, with internal tab 52 inside prosthesis opening 54, exterior tab 50 may be pushed over the top surface of opposing fold 46, 48. Exterior tab 50 may be held in place by surgeon's hand, sealed to opposing fold 46, 48 with surgical tape, heat seal, instant glue, or other forms of seals. Adhered seal 50 opposes prosthesis opening 54 and joins initial fold 48 and base fold 46.

Figure 10:
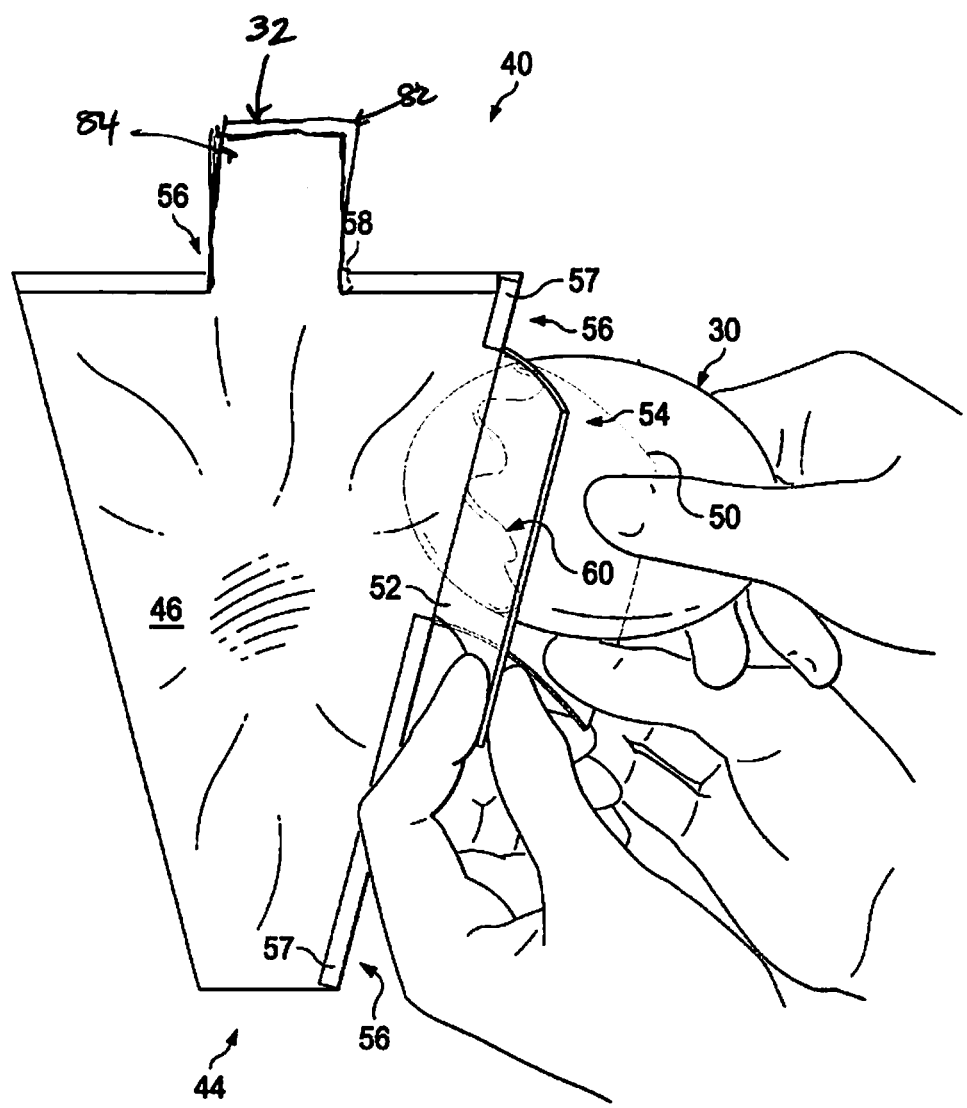
FIG. 10 depicts a front perspective view of a prosthesis bag with an implant being inserted through the prosthesis opening according to an embodiment of the present disclosure.

As illustrated in FIG. 10, in the preferred embodiment, liquid lubricant 60 surrounds breast implant 30 inside prosthesis bag 40. A coating of surgical lubricant 60 may be used on the inner surface of prosthesis bag 40. As an alternative, insertion device 40 may be provided with a coating that becomes slick when wet. In still another alternative, prosthesis 30 may be provided with a slick surface, such as surgical lubricant 60. The surgeon also has the option of applying lubricant 60 to prosthesis 30 directly before inserting into prosthesis bag 40. Lubricant 60 may also act as an antibiotic solution.

After lubrication, breast implant 30 is inserted into device 40 by the surgeon and nurse. To do so, the nurse opens prosthesis opening 54 by separating tabs 50, 52, and the surgeon slides prosthesis 30 through prosthesis opening 54. The team would then fold internal tab 52 into prosthesis opening 54 to prevent breast implant 30 from moving back out of opening 54. Exterior tab 50 may be left extended or folded over opposing fold 46, 48. If desired, exterior tab 50 may be sealed to opposing fold 46, 48. In a preferred embodiment inserting prosthesis 30 into prosthesis bag 40 would be completed prior to inserting retractor 70 into patient incision 20. However, a surgeon could perform this step while bag 40 is inserted in incision 20.

The surgical team may insert lubricant 60 in prosthesis opening 54 and/or through the lubricant instillation opening 32. Liquid lubricant 60 surrounds breast implant 30 inside prosthesis bag 40. An antibiotic solution may be used as lubricant 60.

Figure 11:
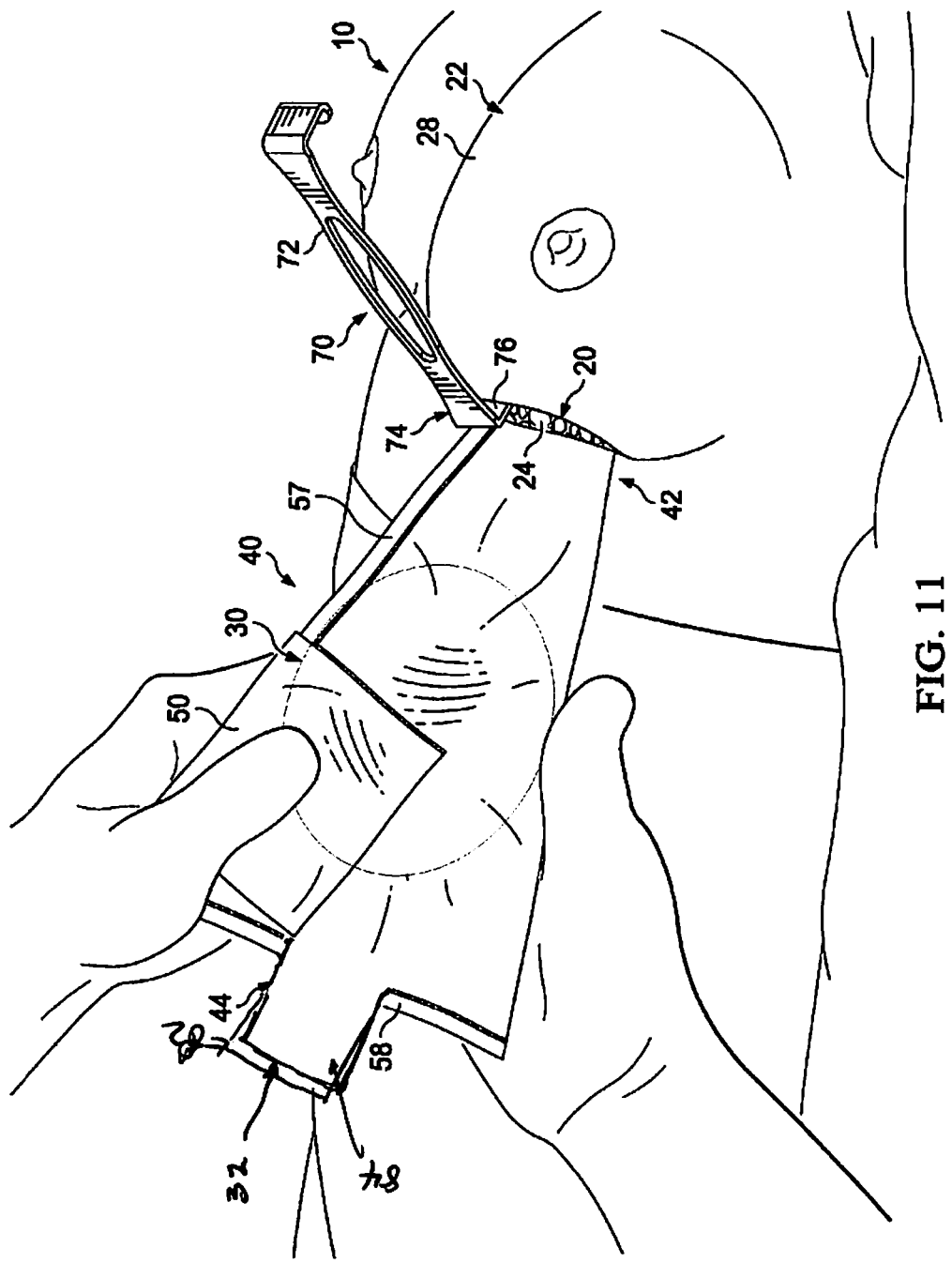
FIG. 11 depicts a left-side perspective view of a prosthesis bag with the proximal end inserted into the left patient incision according to an embodiment of the present disclosure.

FIG. 11 shows patient 10 positioned in a supine position prior to incision 20 being made in the patient's skin tissue 28. In the figure, incision 20 is cut in the right-side inferior breast 22 crease. With incision 20 opened, the surgeon then forms pocket 24 in one of two places under breast 22: subglandular (between breast 22 tissue and pectoralis muscle) or subpectoral (under the pectoralis muscle). Pocket 24 is sized to match prosthesis 30 diameter. By manipulating retractor handle 72, retractor handle proximal end 74 and retractor proximal lip 76 are inserted into incision 20 to both retract incision 20 and hold incision 20 open.

Retractor 70 assembly comprises handle 72 located in the center, retractor handle proximal end 74, and retractor handle proximal end lip 76. Retractor 70 may have various shapes and sizes to match the particular application or surgeon preferences. Handle 72 of retractor 70 is bent or angled on the ends relative to the intermediate portion. Proximal end 74 of retractor 70 has lip 76 that is angled relative to end 74. Retractor 70 is made of metal, such as stainless steel but may also be manufactured in a surgical plastic in some embodiments of the present disclosure.

Retractor proximal end 74 is structured and arranged to be inserted through incision 20 into pocket 24 of patient 10. Proximal end lip 76 helps maintain proximal end 74 of retractor 70 beneath skin tissue 28 of patient 10.

Retractor 70 extends anteriorly from prosthesis bag 40, so as not to interfere with the surgeon manipulating ban 40, with the proximal ends of retractor 74 and proximal end lip 76 inserted into incision 20 and located under skin tissue 28 and moved to retract incision 20. Proximal end 42 of prosthesis bag 40 may be lubricated with lubricant 60 and inserted into to open incision 20.

Prosthesis bag 40, distal to incision 20, is squeezed and/or twisted to force prosthesis 30 toward proximal end 42 of prosthesis bag 40 and into pocket 24. Prosthesis 30 deforms to fit through proximal opening 42. Once prosthesis 30 is located inside pocket 24, retractor 70 is removed from incision 20, followed by bag 40. Incision 20 is then closed. If prosthesis bag 40 is designed for reuse, they are subjected to sterilization procedures. If bag 40 is designed for single use, they are disposed of.

Implant 30 is subject to damage if implant 30 is mishandled. Possible mishandling includes subjecting implant 30 to undue stresses or pressures, such as may be caused by attempting to squeeze implant 30 through proximal end 42 that is too small, and folding of the external silastic shell, internal fracture of the cohesive silicone gel. A surgeon may make incision 20 in patient 10 that is too short for implant 30 and thus too much force is required to squeeze implant 30 into pocket 24. With this prosthesis bag 40, implant 30 is protected from damage by the provision an adequate skin incision length and of properly sized proximal end 42. The major complication with implants 30 is capsular contracture thought to be due to sub-clinical infection. Sub-clinical infection is most likely caused by pushing implant 30 through skin incision 20, dragging natural skin 28 bacteria (still present after proper skin 28 preparations) into pocket 24 surgically created for implant 30. Use of device 40 prevents implant 30 from coming in contact with skin tissue 28 during the insertion process.

Figure 12:
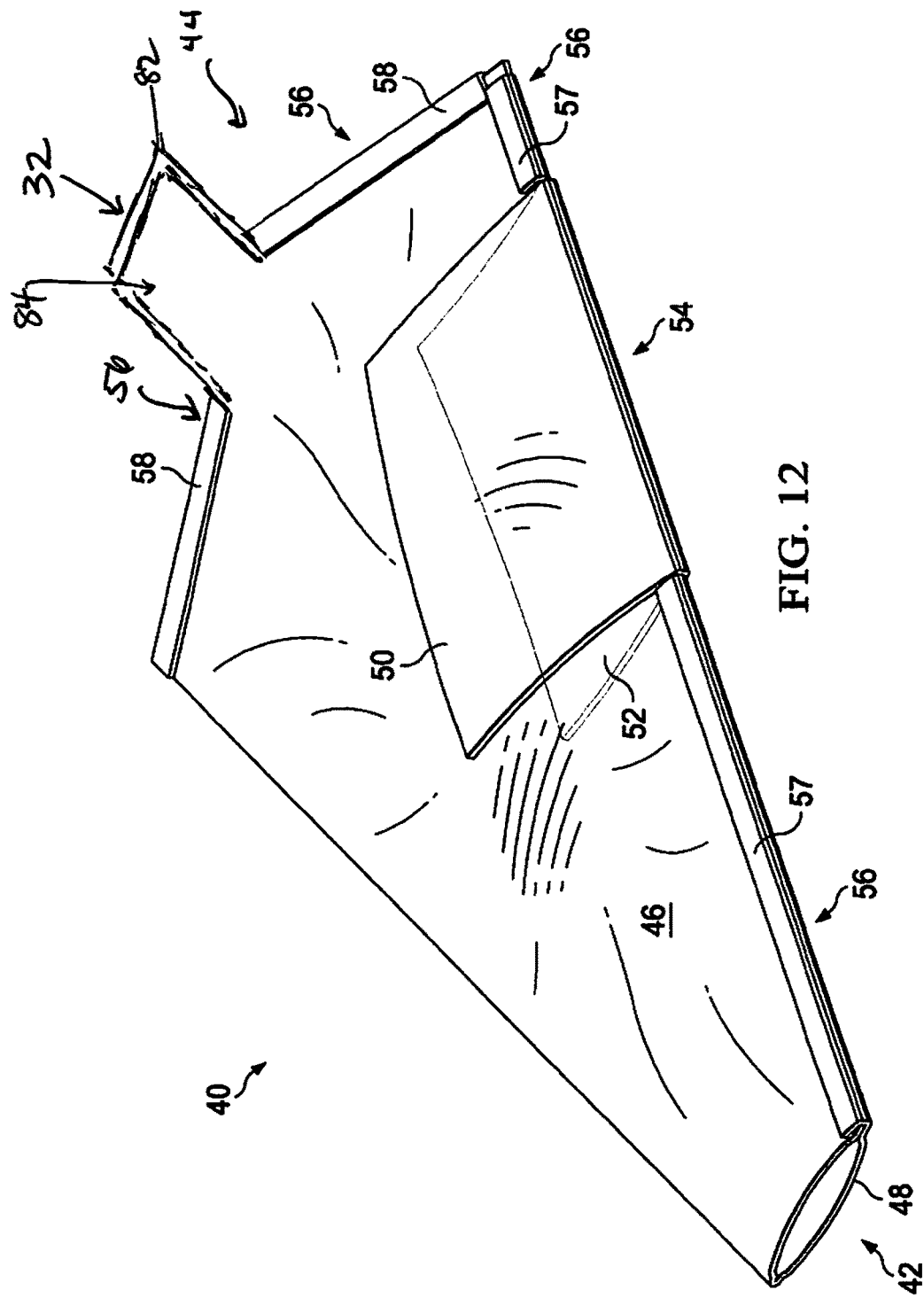
FIG. 12 depicts a top side perspective view of a pentagon prosthesis bag showing a three-sided distal end seal tuck according to an embodiment of the present disclosure.

Distal end 44 of prosthesis bag 40 may be of any shape desirable for efficient manufacturing and/or effective use of bag 40. FIG. 12 demonstrates bag 40 shaped as an irregular pentagon with two (2) angles formed in the distal end seal tuck. This improves manufacturing efficiency in a tuck folding machine versus rounded distal end 44. Sealed distal end 58 may also be designed to improve manipulating bag 40. Small tabs or flaps 82, 84 are included, where—when separated—a small opening is revealed through which the lubricant can be instilled on the inside of the device.

Figure 13:
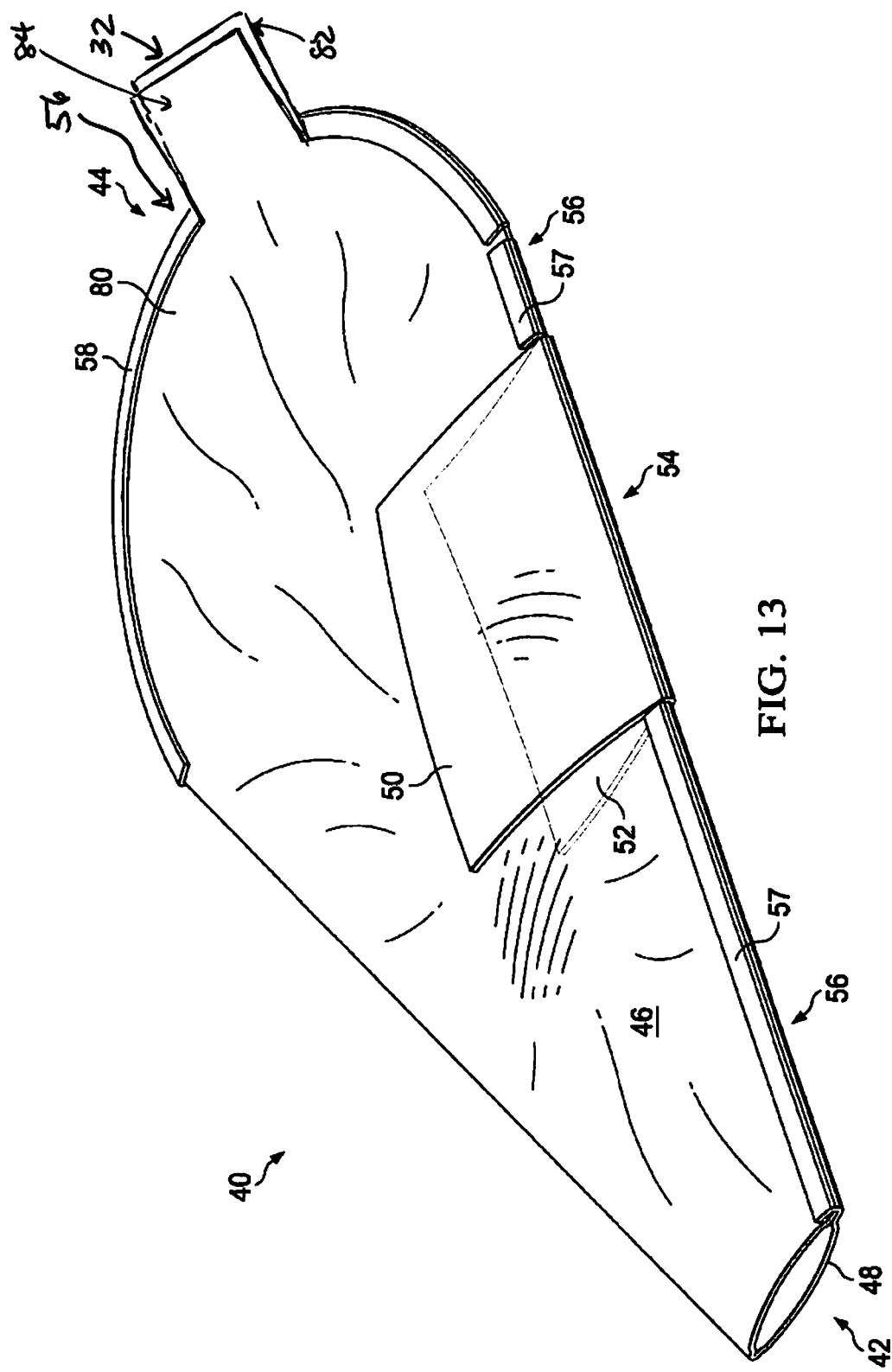
FIG. 13 depicts a top-side perspective view of a pentagon prosthesis bag showing a three-sided distal end seal tuck according to an embodiment of the present disclosure.
Figure 14:
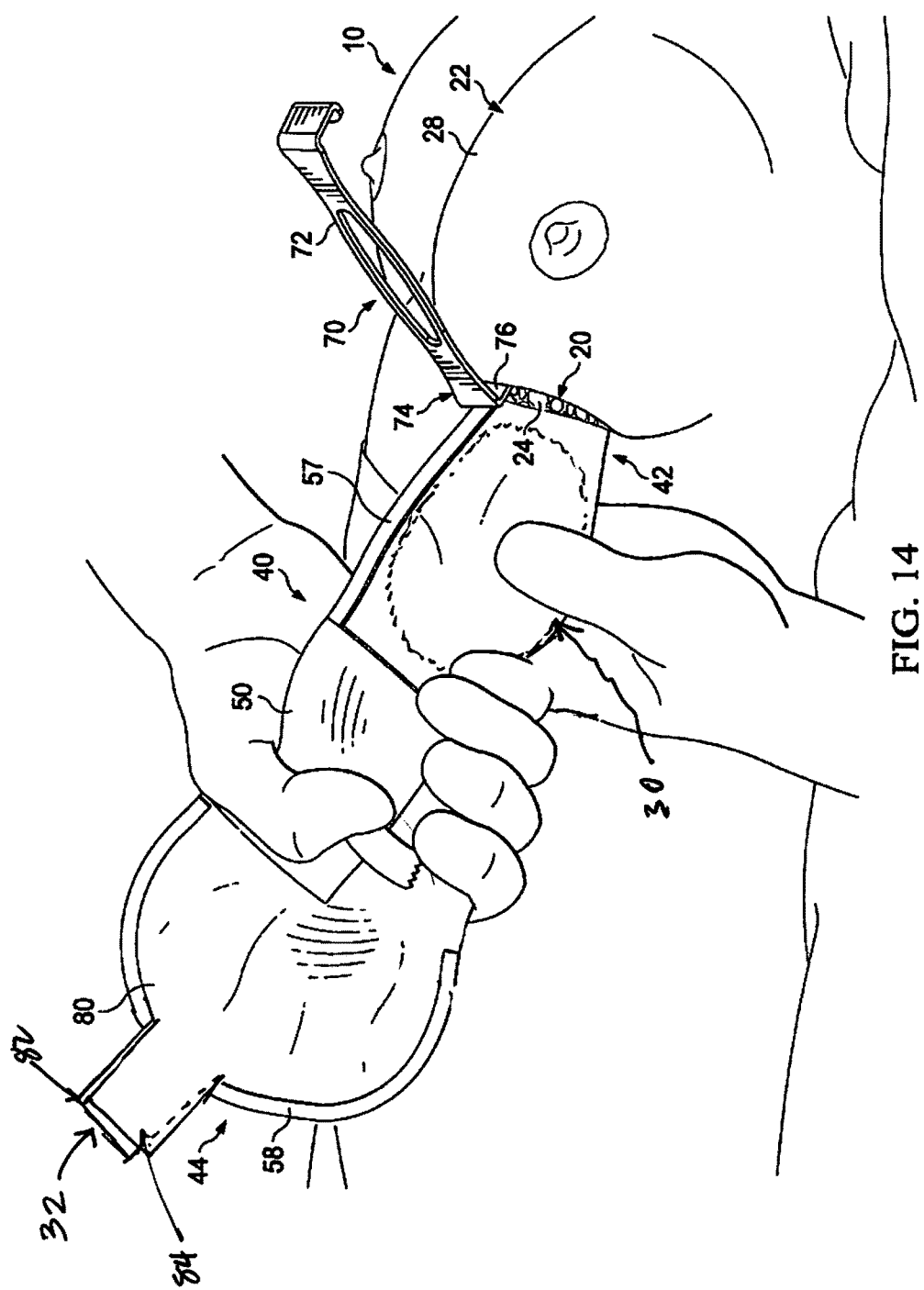
FIG. 14 depicts a top-side perspective view of a pentagon prosthesis bag with a distal pocket proximally to the distal end seal tuck according to an embodiment of the present disclosure.

In FIGS. 13-14, the sealed distal end is rounded to form pouch 80. FIG. 13 shows a top-side perspective of rounded distal end seal tuck 58 surrounding pouch 80. FIG. 14 demonstrates pouch 80 in use by the surgeon where the external tab is sealed to bag 40 with surgical tape.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

In the foregoing description, and the following claims, method steps and/or actions are described in a particular order for the purposes of illustration. It should be appreciated that in alternate embodiments, the method steps and/or actions may be performed in a different order than that described. Additionally, the methods described above may be embodied in machine-executable instructions stored on one or more machine-readable mediums, such as disk drives, thumb drives or CD-ROMs. The instructions may be used to cause the machine (e.g., computer processor) programmed with the instructions to perform the method. Alternatively, the methods may be performed by a combination of hardware and software. While illustrative and presently preferred embodiments of the present disclosure have been described in detail herein, it is to be understood that the inventive concepts may be otherwise variously embodied and employed, and that the appended claims are intended to be construed to include such variations, except as limited by the prior art.

Benefits, other advantages, and solutions to problems have been described herein with regard to specific embodiments. However, the advantages, associated benefits, specific solutions to problems, and any element(s) that may cause any benefit, advantage, or solution to occur or become more pronounced are not to be construed as critical, required, or essential features or elements of any or all the claims of the disclosure. As used herein, the terms "comprises", "comprising", or any other variation thereof, are intended to cover a non-exclusive inclusion, such that a process, method, article, or apparatus composed of a list of elements that may include other elements not expressly listed or inherent to such process, method, article, or apparatus.

Advantages

From the description above, a number of advantages become evident for the "Sealed Distal End Prosthesis Insertion Bag," The present disclosure provides all new benefits for participating parties including manufacturers, patients and surgeons:

a) allows patients a lower risk of complications;
b) allows patients to be under anesthesia for a shorter period of time;
c) allows surgeons to prevent contamination of the implant by inadvertent extrusion of implant because of a sealed distal end;
d) allows surgeons to eliminate damage to the implant during the insertion process;
e) allows surgeons a simplified insertion process; and
f) allows surgeons to perform a faster implant surgery.

The invention claimed is:

1. An apparatus for inserting a prosthesis through an incision into a surgical pocket, comprising:
   a. a breast implant;
   b. a prosthesis bag comprising a prosthesis opening, a proximal opening to allow breast implants to exit and a sealed distal end to prevent the breast implants from exiting, the prosthesis opening surrounded by tabs, the prosthesis bag being semi-rigid and structured and arranged to receive the breast implant through the prosthesis opening, the prosthesis bag assembled with tab-side seal tucks and a distal end seal tuck;
   c. a retractor device, the retractor having a proximal end that is adjacent to the proximal opening and are structured and arranged to engage an edge of a surgical pocket opening, the proximal end being fixed relative to the proximal end of the prosthesis bag.

2. A method of claim 1, wherein said seal distal end comprises a two-sided distal end seal tuck.

3. An apparatus for inserting a prosthesis through an incision into a surgical pocket, comprising:
   a. a breast implant;
   b. a prosthesis bag comprising a prosthesis opening, a proximal opening to allow breast implants to exit and a sealed distal end to prevent the breast implants from exiting, the seal distal end forming a distal pocket, the prosthesis opening surrounded by tabs, the prosthesis bag being semi-rigid and structured and arranged to receive the breast implant through the prosthesis opening, the prosthesis bag assembled with tab-side seal tucks and a distal end seal tuck;

c. a retractor device, the retractor having a proximal end that is adjacent to the proximal opening and are structured and arranged to engage an edge of a surgical pocket opening, the proximal end being fixed relative to the proximal end of the prosthesis bag.

4. An apparatus for inserting a prosthesis through an incision into a surgical pocket, comprising: an initial fold abutted to a base fold along the sides opposing the tabs; the initial fold folded over the base fold along the abutted edge; a tab-side seal tuck from the tab to the proximal end; a tab-side seal tuck from the tab to the distal end; a distal end seal tuck from the abutment to the tab-side seal tuck;

whereby a prosthesis bag is formed with a prosthesis opening and a proximal opening.

5. An apparatus for inserting a prosthesis through an incision into a surgical pocket, comprising: an initial fold abutted to a base fold along the sides opposing the tabs; the initial fold folded over the base fold along the abutted edge; a tab-side seal tuck from the tab to the proximal end; a tab-side seal tuck from the tab to the distal end; a distal end seal tuck from the abutment to the tab-side seal tuck; a distal pocket formed by the distal end seal tuck; whereby a prosthesis bag is formed with a prosthesis opening and a proximal opening.

* * * * *